(12) United States Patent
Randolph et al.

(10) Patent No.: US 7,956,227 B2
(45) Date of Patent: Jun. 7, 2011

(54) OLIGOMERIZATION OF HYDROCARBONS

(75) Inventors: Bruce B. Randolph, Bartlesville, OK (US); Jason J. Gislason, Lake Jackson, TX (US); M. Bruce Welch, Greenbrier, AR (US); Richard L. Anderson, Bartlesville, OK (US); Dhananjay B. Ghonasgi, Bartlesville, OK (US); Robert W. Morton, Bartlesville, OK (US); Roland Schmidt, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 720 days.

(21) Appl. No.: 11/951,863

(22) Filed: Dec. 6, 2007

(65) Prior Publication Data

US 2009/0149684 A1 Jun. 11, 2009

(51) Int. Cl.
*C07C 2/12* (2006.01)

(52) U.S. Cl. ........ 585/518; 585/300; 585/304; 585/310; 585/314; 585/329; 585/330; 585/502; 585/519; 585/520; 585/530; 585/532; 585/533

(58) Field of Classification Search .................. 585/502, 585/518, 519, 520, 530, 532, 533
See application file for complete search history.

(56) References Cited

U.S. PATENT DOCUMENTS

| | | | |
|---|---|---|---|
| 3,291,855 A | 12/1966 | Haensel | |
| 3,960,978 A | 6/1976 | Givens et al. | |
| 4,021,502 A | 5/1977 | Plank et al. | |
| 4,024,203 A | 5/1977 | Torck et al. | |
| 4,150,062 A | 4/1979 | Garwood et al. | |
| 4,188,501 A | 2/1980 | Rycheck et al. | |
| 4,268,700 A * | 5/1981 | Dang Vu et al. | 585/302 |
| 4,293,728 A | 10/1981 | Montgomery | |
| 4,377,393 A | 3/1983 | Schleppinghoff | |
| 4,413,153 A | 11/1983 | Garwood et al. | |
| 4,414,423 A | 11/1983 | Miller | |
| 4,423,269 A * | 12/1983 | Miller | 585/533 |
| 4,454,367 A | 6/1984 | Sakurada et al. | |
| 4,456,779 A | 6/1984 | Owen et al. | |
| 4,542,247 A | 9/1985 | Chang et al. | |
| 4,636,225 A * | 1/1987 | Klein et al. | 95/120 |
| 4,675,461 A | 6/1987 | Owen et al. | |
| 4,727,203 A * | 2/1988 | Hamilton, Jr. | 585/328 |
| 4,749,820 A | 6/1988 | Kuo et al. | |
| 4,777,316 A | 10/1988 | Harandi et al. | |
| 4,788,366 A | 11/1988 | Harandi et al. | |
| 4,902,847 A * | 2/1990 | Juguin et al. | 585/533 |
| 4,925,995 A | 5/1990 | Robschlager | |
| 4,939,314 A | 7/1990 | Harandi et al. | |

(Continued)

FOREIGN PATENT DOCUMENTS

WO WO 01/40695 6/2001

OTHER PUBLICATIONS

Roland, et al., "Zeolites" in Ullmann's Encyclopedia of Industrial Chemistry, Wiley-VCH, 2000, available on-line Jun. 15, 2000.*

(Continued)

*Primary Examiner* — In Suk Bullock
*Assistant Examiner* — Bradley Etherton

(57) ABSTRACT

Methods of oligomerizing hydrocarbons are disclosed. These methods include contacting olefins with an oligomerization catalyst in an oligomerization zone under oligomerization reaction conditions.

24 Claims, 2 Drawing Sheets

U.S. PATENT DOCUMENTS

| | | | |
|---|---|---|---|
| 4,971,606 A * | 11/1990 | Sircar et al. | 95/97 |
| 4,973,790 A * | 11/1990 | Beech et al. | 585/533 |
| 5,019,357 A | 5/1991 | Harandi et al. | |
| 5,043,517 A | 8/1991 | Haddad et al. | |
| 5,053,579 A | 10/1991 | Beech, Jr. et al. | |
| 5,057,640 A * | 10/1991 | Chang et al. | 585/533 |
| 5,177,282 A | 1/1993 | Nierlich et al. | |
| 5,198,099 A | 3/1993 | Trachte et al. | |
| 5,234,873 A * | 8/1993 | Basset et al. | 502/66 |
| 5,405,814 A | 4/1995 | Beech, Jr. et al. | |
| 5,430,220 A | 7/1995 | Khare et al. | |
| 5,624,547 A | 4/1997 | Sudhakar et al. | |
| 5,672,800 A | 9/1997 | Mathys et al. | |
| 5,847,252 A * | 12/1998 | Stine et al. | 585/330 |
| 5,873,994 A | 2/1999 | Drake et al. | |
| 6,281,401 B1 | 8/2001 | Randolph | |
| 6,500,999 B2 | 12/2002 | Di Girolamo et al. | |
| 6,864,398 B2 | 3/2005 | O'Rear | |
| 6,884,914 B2 * | 4/2005 | Mathys et al. | 585/324 |
| 2008/0029437 A1 * | 2/2008 | Umansky et al. | 208/238 |

OTHER PUBLICATIONS

Montemayor, Distillation and Vapor Pressure Measurements in Petroleum Products: MNL 51, 2008, ASTM International, available on-line at www.knovel.com.*

Lide, CRC Handbook of Chemistry and Physics, 91 ed., 2011 Internet Version, D. R. Lide, ed.*

* cited by examiner

OLIGOMERIZATION OF HYDROCARBONS

FIELD OF INVENTION

The present invention relates generally to processing hydrocarbon-containing streams. In one aspect, the invention concerns processes for the oligomerization of hydrocarbon-containing streams.

BACKGROUND

Much of the refinery related research over the past 5-10 years has been directed at converting light naphtha streams that are too high in Reid Vapor Pressure (RVP) for large volume use in gasoline, to higher molecular weight gasoline and diesel range compounds with lower RVP values. The desire for such capabilities continues to grow with downward pressure on gasoline RVP to reduce fugitive emissions into the atmosphere and as the use of ethanol in the gasoline pool increases.

The Reid Vapor Pressure is a measure of the vapor pressure of gasoline, volatile crude oils, and other volatile petroleum products determined at approximately 38° C. In the past decades, the Environmental Protection Agency (EPA) imposed regulations controlling hydrocarbon emissions from fuel sources in order to reduce ground ozone levels. Volatile organic compounds (VOCs) from evaporative sources are a major source for the generation of this urban ozone. Thus, restrictions on light hydrocarbon streams become more and more stringent forcing the lightest components out of the available fuel pool. With increased ethanol blending, this problem will be exacerbated since blending ethanol requires a lower RVP base stock to achieve overall final fuel RVP specifications.

In 2012, about four hundred ninety thousand barrels per day of renewable fuels (mainly comprising ethanol) will be mandated. The use of ethanol in reformulated gasoline (RFG) will not be optional for many refiners as they will need to use it to achieve octane. If by 2012 all the gasoline pool is mandated to be RFG then the displaced C5 would further double assuming the required volume of renewables remains constant. In addition, these objectives must be met without negatively impacting other fuel parameters such as octane and distillation points.

SUMMARY OF THE INVENTION

In accordance with the present invention, a process has been discovered which comprises, consists of, or consists essentially of
  (1) separating a hydrocarbon stream in a separation zone to provide a separated product comprising olefins;
  (2) contacting the olefins with at least one guard bed to provide pretreated olefins,
  (3) contacting the pretreated olefins with a catalyst comprising a zeolite in an oligomerization zone under oligomerization reaction conditions to form an oligomerization product; and
  (4) recovering the oligomerization product.
Another embodiment of the invention is a process which comprises, consists of, or consists essentially of:
  (1) dehydrogenating a hydrocarbon feedstock comprising paraffins in a dehydrogenation zone under dehydrogenation conditions to form a dehydrogenation product comprising olefins;
  (2) oligomerizing the olefins in an oligomerization reaction zone under oligomerization reaction conditions to form an oligomerization product comprising of oligomers and gasoline;
  (3) separating a first component comprising compounds selected from the group consisting of compounds with 8 carbon atoms per molecule and compounds with 10 carbon atoms per molecule from the oligomerization product in a first separation zone;
  (4) returning said first component to an oligomerization reaction zone;
  (5) separating a second component comprising compounds selected from the group consisting of compounds with 4 carbon atoms per molecule and compounds with 5 carbon atoms per molecule from the oligomerization product in a second separation zone;
  (6) returning the second component to said dehydrogenation zone;
  (7) separating a third component comprising compounds with at least 12 carbon atoms per molecule from the oligomerization product in a third separation zone; and
  (8) transferring the third component to a hydrotreating zone.

Still another embodiment of the invention is a process which comprises, consists of, or consists essentially of:
  (1) contacting a feed comprising, consisting of, or consisting essentially of a paraffin, an internal olefin and an alpha olefin with an oligomerization catalyst in a oligomerization reaction zone under oligomerization reaction conditions to provide an oligomerization product; and
  (2) recovering said oligomerization product.

Other objects and advantages will become apparent from the detailed description and the appended claims.

DETAILED DESCRIPTION OF THE INVENTION

Figure 1:
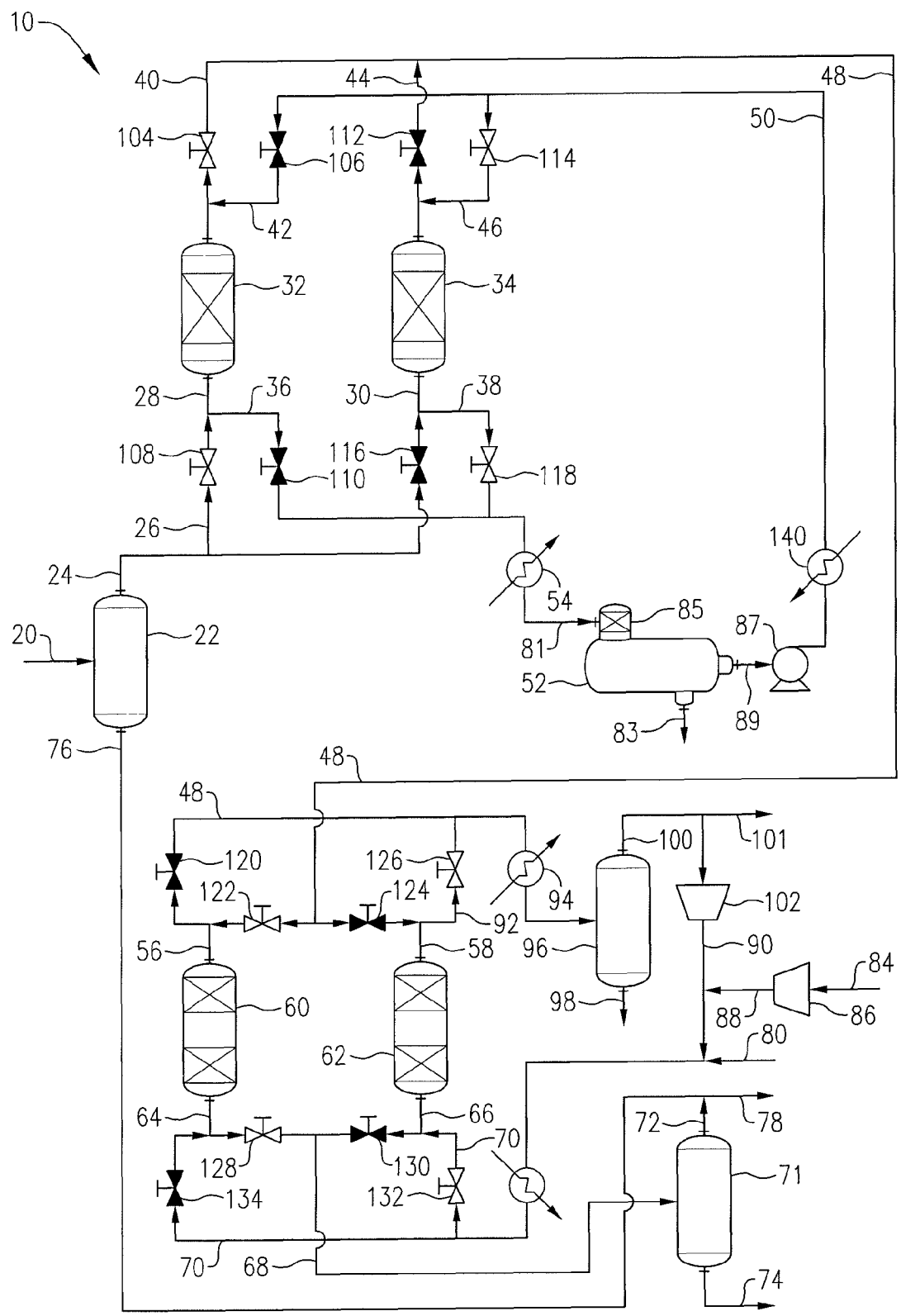
FIG. 1 depicts an oligomerization process system.

One embodiment of the present invention is a process comprising, consisting of, or consisting essentially of:
  (1) separating a hydrocarbon stream in a separation zone to provide a separated product comprising olefins;
  (2) contacting said olefins with at least one guard bed to provide pretreated olefins,
  (3) contacting said pretreated olefins with a catalyst comprising a zeolite in an oligomerization zone under oligomerization reaction conditions to form an oligomerization product; and
  (4) recovering the oligomerization product.

Any zeolite-containing catalyst which is effective for the oligomerization of hydrocarbons can be used. Generally, the molar ratio of $SiO_2$ to $Al_2O_3$ in the crystalline framework of the zeolite is in the range of from about 10:1 to about 150:1. The molar ratio of $SiO_2$ to $Al_2O_3$ in the zeolite framework can also be in the range of from about 30:1 to about 100:1. Examples of zeolites that can be used include, but are not limited to mordenites. Examples of mordenites that can be used include but are not limited to Mordenite 40, Mordenite 90 and their hydrogen-promoted counterparts.

Any olefin can be oligomerized by the process of the present invention. Generally, the olefins have in the range of from 2 to 20 carbon atoms per molecule. The olefins can also have in the range of from 3 to 6 carbon atoms per molecule, and, additionally, the olefins can have 4 to 5 carbon atoms per molecule.

Generally, the oligomerization reaction conditions in the oligomerization reaction zone include a temperature in the range of from about 35° C. to about 260° C. The temperature can also be in the range of from about 65° C. to about 150° C., and, additionally, the temperature can be in the range of from 90° C. to 130° C.

The oligomerization reaction conditions also include a pressure in the range of from about 100 psi to about 800 psi. The pressure can also be in the range of from about 300 psi to about 500 psi, and, additionally, the pressure can range from 200 psi to 600 psi. The desired pressure maintains the process stream in the liquid form.

Before contacting the zeolite catalyst with olefins in an oligomerization zone, the zeolite can optionally be treated with one or more metal compounds in order to increase the acidity of the zeolite. The zeolite can be treated with compounds containing metals selected from the group consisting of zinc, cadmium, copper, silver, gold, gallium, indium, silicon, germanium, and tin. Generally, the compound contains zinc or tin. The metal compound can be incorporated into or onto the zeolite. One method of incorporating is to impregnate using any standard incipient wetness impregnation technique (i.e. essentially completely or partially filling the pores of a substrate material with a solution of the incorporating elements) for impregnating a substrate. This method uses an impregnating solution comprising the desirable concentration of a metal containing compound. Metal containing compounds that can be used include, but are not limited to, metal salts such as metal chlorides, metal nitrates, metal sulfates, and the like and combinations thereof. Metal-containing organic compounds can also be used. Examples of metal containing compounds useful in the present invention include, but are not limited to, zinc nitrate and dibutyltin bis(2-ethylhexanoate). An impregnating solution comprises a solution formed by dissolving a metal containing compound in a solvent such as water, alcohols, esters, ethers, ketones, hydrocarbons and combinations thereof. The concentration of the metal in the solution can be in the range of from about 0.01 gram of metal per gram of solution to about 0.9 grams of metal promoter per gram of solution.

In order to reduce potential catalyst poisons, it is desirable to pass the olefins through a series of one or more guard beds before the olefins are contacted with a zeolite catalyst. The guard beds are generally arranged in a series containing from one to four separate guard beds. The guard beds can contain a compound selected from the group consisting of a molecular sieve, silica gel and combinations thereof. The molecular sieves are commonly either 3 Angstrom or 13× molecular sieves. The guard beds can contain any combination of 3 Angstrom molecular sieves, silica gel, and 13× molecular sieves. The guard beds can be regenerated by any suitable regeneration stream. The guard beds can be regenerated by contact with air or with a gaseous organic compound. The gaseous organic compound can be for example, gaseous isobutane. The guard bed regeneration process comprises, consists of, or consists essentially of the steps of: (a) contacting a regeneration stream with the guard bed to form an adsorbed stream, (b) condensing the adsorbed stream to form a condensed stream, (c) adding water to the condensed stream to form a waste stream, and (d) disposing of the waste stream.

The zeolite catalyst can also be regenerated. The catalyst can be regenerated by any suitable regeneration stream. Examples of suitable regeneration streams include, but are not limited to, air, nitrogen, supercritical isobutane, and other light hydrocarbons. Generally the regeneration conditions include a regeneration pressure in the range of from about 500 psi to about 1500 psi. The regeneration pressure can also be in the range of from about 529 psi to about 800 psi. The pressure can additionally be in the range of from 529 psi to 650 psi. The regeneration temperature depends on which regeneration stream is being used. Generally the temperature is in the range of from about 50° C. to about 900° C. For example, when air is used, the temperature can be in the range of from about 250° C. to about 650° C., and additionally can be in the range of from 350° C. to 550° C. When nitrogen is used, the temperature can be in the range of from about 100° C. to about 500° C., and additionally can be in the range of from 200° C. to 400° C. When supercritical isobutane is used, the temperature can be in the range of from about 135° C. to about 500° C., and additionally can be in the range of from 135° C. to 300° C.

The process of the first embodiment of the invention can also further comprise: (5) separating compounds comprising n-alkenes from the oligomerization product, (6) contacting the compounds comprising n-alkenes with an isomerization catalyst in an isomerization reaction zone under isomerization conditions to form an isomerization product; and (7) returning the isomerization product to the oligomerization zone.

FIG. 1 further illustrates this embodiment of the invention.

Referring to FIG. 1, system 10 is illustrated in the following manner: a hydrocarbon feed enters separator 22 via conduit 20. In separator 22, oligomers, such as for example either C4s or C5s are separated from the remainder of the feed. The remainder of the feed, minus either the C4s or C5s, exits separator 22 via conduit 76 and passes on to further blending via conduit 78. Meanwhile, the separated C4 or C5 stream (referred to hereinafter as the "C4/C5 stream") exits separator 22 via conduit 24 and passes through conduit 26 to guard bed 32, which the C4/C5 stream enters via conduit 28. Guard bed 32 contains compounds which can pretreat the C4/C5 stream before the C4/C5 stream enters the oligomerization zone. The C4/C5 stream leaves the guard bed via conduit 40 and then travels via conduit 48 to oligomerization reactor 60, which the stream enters via conduit 56. The C4/C5 stream is then oligomerized, and exits oligomerization reactor 60 via conduit 64. The oligomerization product then travels via conduit 68 for the desired further processing. One option is to pass the oligomerization product to fractionator column 71 for further separation. The fractionated product then exits fractionator column 71 via conduits 72 and 74, moving on to any desired further blending.

Meanwhile, guard bed 34 and reactor 62 go through a regeneration cycle. Regeneration fluid in conduit 50 passes into guard bed 34 via conduit 46. The regeneration fluid removes the water that was collected in guard bed 34 and both the regeneration fluid and water exit guard bed 34 via conduit 38 and pass through cooler 54 and then to vessel 52 via conduit 81. Vessel 52 separates the regeneration fluid from water and other impurities. Additional water can enter vessel 52 via opening 85 to help with this process. The water and other impurities exit vessel 52 via conduit 83. The now separated regeneration fluid exits vessel 52 via conduit 50, passes through pump 87 which raises the pressure, and continues via conduit 50, is vaporized by heater 140 and then enters guard bed 34 via conduit 46 to begin the regeneration process once more.

While reactor 60 is active, reactor 62 is in the regeneration phase. Air enters air compressor 86 via conduit 84. The air then travels via conduit 88, mixes with recycle gas in conduit 90, then joins a nitrogen stream in conduit 80. The air/nitrogen stream then travels to conduit 70 and enters reactor 62 via conduit 66. The stream exits reactor 62 via conduit 58 and travels via conduit 92 to cooling unit 94, then to vessel 96, where condensed water is knocked out of the stream, exiting vessel 96 through conduit 98. Inert gases leave vessel 96 via conduit 100 then conduit 101. Some off gases are purged, while regenerator off-gas passes through recycle compressor 102 and back to conduit 90. In this process, valves 104, 108, 114, 118, 122, 126, 128 and 132 are open while valves 106, 110, 112, 116, 120, 124, 130 and 134 are closed. After the desired regeneration is finished the open valves can be closed and the closed valves can be opened, in order to enable guard bed 34 and reactor 62 to be in the process phase, while guard bed 32 and reactor 60 enter the regeneration phase. In this process, the C4/C5 stream enters guard bed 34 via conduit 30, and exits via conduit 44, and subsequently enters reactor 62 via conduit 58 and exits reactor 62 via conduit 66. Meanwhile, regeneration fluid enters guard bed 32 via conduit 42 and exits via conduits 28 and 36. An air/nitrogen regeneration stream can enter reactor 60 via conduit 64 and exits via conduit 56. The rest of the process continues to operate in the manner described above.

Another embodiment of the invention is a process comprising, consisting of, or consisting essentially of the steps of:
(1) dehydrogenating a hydrocarbon feedstock comprising paraffins in a dehydrogenation zone under dehydrogenation conditions to form a dehydrogenation product comprising olefins;
(2) oligomerizing said olefins in an oligomerization reaction zone under oligomerization reaction conditions to form an oligomerization product comprising of oligomers and gasoline components;
(3) separating a first component comprising compounds selected from the group consisting of compounds with 8 carbon atoms per molecule and compounds with 10 carbon atoms per molecule from the oligomerization product in a first separation zone;
(4) returning said first component to an oligomerization reaction zone;
(5) separating a second component comprising compounds selected from the group consisting of compounds with 4 carbon atoms per molecule and compounds with 5 carbon atoms per molecule from the oligomerization product in a second separation zone;
(6) returning the second component to the dehydrogenation zone;
(7) separating a third component comprising compounds with at least 12 carbon atoms per molecule from the oligomerization product in a third separation zone; and
(8) transferring the third component to a hydrotreating zone. The gasoline components can also be separated from the oligomerization product so it can be put to further use.

Generally, dehydrogenation conditions comprise a reaction temperature in the range of from about 150° C. to about 1000° C. The reaction temperature can also be in the range of from about 200° C. to about 650° C., and, additionally, the reaction temperature can be in the range of from about 300° C. to about 650° C.

The dehydrogenation product comprises olefins having either 4 or 5 carbon atoms per molecule. These olefins are then oligomerized in an oligomerization zone under oligomerization reaction conditions.

The oligomerization reaction conditions are the same as described above.

The oligomerization catalyst used in this embodiment can be any catalyst that is used in the previous embodiment, as described above. The catalyst can also be pre-treated with a metal-containing compound, such as, for example, a zinc or tin-containing compound, as described above.

The oligomerization process of step (2) produces a product comprised of oligomers and gasoline components. If the dehydrogenation product comprises C4s, then the oligomerization product comprises of compounds with 4, 8, and 12 or more carbon atoms per molecule. If the dehydrogenation product comprises C5s, then the oligomerization product comprises of compounds with 5, 10, and 15 or more carbon atoms per molecule. These different compounds are then separated via different separation zones. The compounds with 8 or 10 carbon atoms per molecule are then returned to an oligomerization zone, which can be the same oligomerization zone as in step (2) or a separate one. The compounds with 4 or 5 carbon atoms per molecule which comprise unreacted paraffins are returned to the dehydrogenation zone and the compounds with 12 or more carbon atoms per molecule are sent to a hydrotreating zone for the distillate pool.

Figure 2:
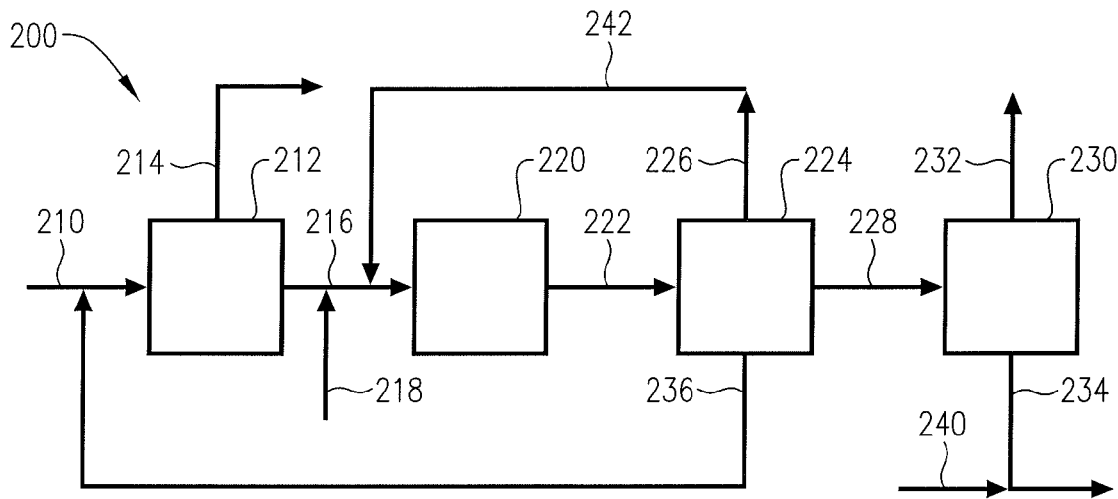
FIG. 2 depicts a hydrocarbon processing and separation system.

FIG. 2 further illustrates this embodiment of the invention.

Referring to FIG. 2, system 200 is illustrated in the following manner: a hydrocarbon stream enters dehydrogenation zone 212 via conduit 210. The hydrocarbons are then dehydrogenated. Dehydrogenation zone 212 can be any suitable dehydrogenation system known in the art. This stream is dehydrogenated to form a mixture of normal butenes and isobutene. Hydrogen and lighter carbon molecules exit dehydrogenation zone 212 via conduit 214. Meanwhile, the dehydrogenation product comprising either C4s or C5s enters oligomerization zone 220 via conduit 216. Other C4 or C5 olefins can join conduit 216 via conduit 218 and thereafter also enter oligomerization zone 220. Oligomerization zone 220 is configured as the system disclosed in FIG. 1 above. The C4 or C5 olefins are oligomerized in oligomerization zone 220 to form olefins containing 8, 10 and 12 or more carbon atoms per molecule (in the case of a C4 feed) or olefins containing 5, 10, and 15 or more carbon atoms per molecule (in the case of a C5 feed). The resulting oligomerization product then passes into separation zone 224 via conduit 222. In separation zone 224, C8+ olefins are separated from C4 olefins or C10+ olefins are separated from C5 olefins. The C4 or C5 olefins leave the separation zone 224 via conduit 226 and are recycled back to the oligomerization zone via conduit 242 which will join conduit 216 to enter oligomerization zone 220. Additionally, alkanes are separated in separation zone 224. These compounds are recycled to the dehydrogenation zone via conduit 236. This conduit joins conduit 210 leading into dehydrogenation zone 212. The C8 or C10 olefins enter separation zone 230 via conduit 228. In separation zone 230, the C12+ compounds are separated from the C8 or C10 olefins. The C8 or C10 olefins exit separation zone 230 via conduit 232 and go on to further gasoline processing. The C12+ compounds exit separation zone 230 via conduit 234 and to then move on to further kerosene or diesel processing. Hydrogen can be added to conduit 234 via conduit 240.

Another embodiment of the invention is a process comprising, consisting of, or consisting essentially of the steps of:
(1) contacting a feed comprising a paraffin, an internal olefin and an alpha olefin with an oligomerization catalyst in a oligomerization reaction zone under oligomerization reaction conditions to provide an oligomerization product; and
(2) recovering the oligomerization product.

Any suitable paraffin, internal olefin and alpha olefin can be used. Examples of suitable paraffins include, but are not limited to propane, isobutanes, isopentanes, and isohexanes. Examples of suitable internal olefins include, but are not limited to, isobutene, isopentenes, and isohexenes. Examples of suitable alpha olefins include, but are not limited to, propene, 1-butene, 1-pentene, and 1-hexene. One example of a suitable feed is a feed comprising isopentane, isobutene, and 1-butene.

Generally, the olefins are present in the feed in an amount in the range of from about 0.1 weight percent to about 100 weight percent based on the total weight of the feed. The alpha olefin can be present in an amount in the range of from about 5 weight percent to about 35 weight percent, and the alpha olefin can also be present in the range of from 10 weight percent to 25 weight percent, based on the total weight of the feed. The internal olefin can be present in an amount in the range of from about 5 weight percent to about 35 weight percent, and the internal olefin can also be present in the range of from 10 weight percent to about 25 weight percent based on the total weight of the feed.

The catalyst used and the oligomerization reaction conditions in the oligomerization zone are the same as in the previous embodiments, as described above.

The following examples are presented to further illustrate this invention and are not to be construed as unduly limiting its scope.

EXAMPLE I

Three different C5 feedstocks were oligomerized by the following process: a mordenite catalyst was placed into a cylindrical reactor tube. A feed was then passed from a feed pump to a series of two guard beds for treatment. The feed was then passed into the reactor tube, where it underwent oligomerization and was afterwards collected in a collection vessel. Table 1 below shows results for three C5 feeds, labeled as Feed 1, Feed 2, and Feed 3. Feed 2 has the highest sulfur content. Table 1 shows weight percent conversion after 4 days of oligomerization. For each feed there was a run with guard bed treatment and a run eliminating the guard bed treatment step.

TABLE I

|  | FEED 1 | | FEED 2 | | FEED 3 | |
| --- | --- | --- | --- | --- | --- | --- |
| Source | Feed | Product | Feed | Product | Feed | Product |
| Dienes, ppmw | 0.2 | NA | 1.1 | NA | <0.1 | NA |
| Sulfur, ppmw | 2.3 | 2.8 | 33 | 27 | 1.4 | 0.0 |
| Nitrogen, ppmw | 1.0 | <0.1 | 1.0 | 0.1 | 0.1 | <0.1 |
| Conversion, wt. % 4 days w/o guard beds | | 48 | | 19 | | 62 |
| Conversion, wt. % 4 days w/o guard beds | | 61 | | 13 | | 62 |

EXAMPLE II

A C5 feedstock was oligomerized by the following process: a 26.25-gram quantity of an H-Mordenite 90 catalyst was placed into a cylindrical reactor tube. The feed was then passed from a feed pump to a series of two guard beds, which contained a 3 Å sieve, silica gel, and a 13× sieve. The feed then passed into the reactor tube, where it then underwent oligomerization and was afterwards collected in a collection vessel. The guard beds were regenerated at 230° C. with dilute air and the catalyst was regenerated with dilute air at 550° C. The reaction system was run for 137.4 hours. The results are shown in Table II below.

TABLE II

| Time on Stream, hrs. | Net Conversion (wt. %) |
| --- | --- |
| 1.8 | 60 |
| 10.7 | 62 |
| 18.9 | 65 |
| 29.5 | 65 |
| 42.4 | 66 |
| 78.3 | 62 |
| 113.7 | 61 |
| 125.7 | 60 |
| 137.4 | 63 |

EXAMPLE III

Figure 3:
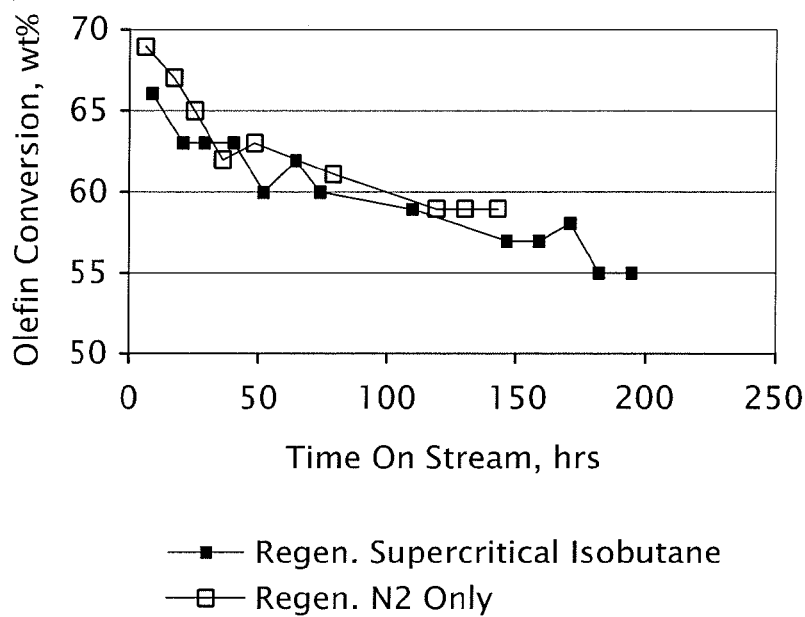
FIG. 3 is a graph plotting the weight percent of olefin conversion vs. time on-stream.

A C5 feedstock was oligomerized by the process of Example II. FIG. 3 shows the results of the regeneration of the mordenite with nitrogen and with supercritical isobutane.

EXAMPLE IV

Control

A C4 feedstock was oligomerized by the following process: 6.5 grams of H-Mordenite 40 catalyst, diluted with a 30 mL volume of 14 grit alundum was placed into a cylindrical reactor tube. The feed was then passed from a feed pump to a series of two guard beds, which contained a 3 Angstrom sieve, silica gel, and a 13× sieve. The feed then passed into the reactor tube, where it then underwent oligomerization and was afterwards collected in a collection vessel. The reaction system ran for about 144.2 hours. The results are shown in Table III below.

TABLE III

| Time on-stream, hrs. | Conversion (wt. %) | Selectivity to $C_8$'s (wt. %) |
| --- | --- | --- |
| 6 | 99.79 | 19.96 |
| 16.5 | 99.36 | 27.72 |
| 23.8 | 91.40 | 40.04 |
| 30.3 | 49.04 | 60.15 |
| 40.4 | 9.55 | 77.70 |
| 64.3 | −0.74 | 90.57 |
| 88.3 | −3.50 | 100.00 |
| 95.9 | −0.96 | 91.18 |
| 102.1 | 3.82 | 82.61 |
| 112.2 | 21.13 | 92.02 |
| 121.7 | 80.04 | 72.36 |
| 125.8 | 90.02 | 69.40 |
| 136.1 | 96.18 | 58.33 |
| 144.2 | 97.88 | 50.77 |

Inventive (Catalyst Treated with Zinc)

An H-Mordenite 40 catalyst was treated with zinc nitrate. A 0.1 gram quantity of zinc nitrate hexahydrate was dissolved in 8 mL of water. The mixture was then heated to a temperature of 250° C to dissolve the zinc nitrate. This mixture was then added to 15 grams of a H-Mordenite 40 catalyst in 3 increments. The catalyst was then dried.

The catalyst was then tested for oligomerization activity with a C4 feed by the following process: 6.5 grams of the catalyst, diluted with a 30 mL volume of 14 grit alundum was placed into a cylindrical reactor tube. The feed was then passed from a feed pump to a series of two guard beds, which contained a 3 Angstrom sieve, silica gel, and a 13× sieve. The feed then passed into the reactor tube, where it then underwent oligomerization and was afterwards collected in a collection vessel. The reaction system ran for about 148 hours. The results are shown in Table IV below.

TABLE IV

| Time on-stream, hrs. | Conversion (wt. %) | Selectivity to C$_8$'s (wt. %) |
|---|---|---|
| 4.7 | 99.90 | 17.64 |
| 14.6 | 99.90 | 23.5 |
| 21.9 | 99.80 | 24.33 |
| 28.6 | 99.70 | 24.85 |
| 29.6 | 98.88 | 30.82 |
| 46.3 | 96.14 | 39.27 |
| 52.3 | 90.35 | 47.23 |
| 62.6 | 71.44 | 61.80 |
| 71.4 | 50.51 | 76.51 |
| 76.4 | 37.60 | 82.61 |
| 93.5 | 23.88 | 91.94 |
| 114.5 | 23.07 | 93.05 |
| 134.3 | 37.70 | 88.37 |
| 141.9 | 43.29 | 89.02 |
| 148 | 52.64 | 86.07 |

Inventive (Catalyst Treated with Tin)

An H-Mordenite 40 catalyst was treated with dibutyltin bis(2-ethylhexanoate). A 0.25 gram quantity of dibutyltin bis(2-ethylhexanoate) was dissolved in 8 mL of acetone. This mixture was heated, and then added to 15 grams of a H-Mordenite 40 catalyst in 3 increments. The catalyst was then dried.

The catalyst was then tested for oligomerization activity with a C4 feed by the following process: 6.5 grams of the catalyst, diluted with a 30 mL volume of 14 grit alundum was placed into a cylindrical reactor tube. The feed was then passed from a feed pump to a series of two guard beds, which contained a 3 Angstrom sieve, silica gel, and a 13× sieve. The feed then passed into the reactor tube, where it then underwent oligomerization and was afterwards collected in a collection vessel. The reaction system ran for about 145.5 hours. The results are shown in Table V below.

TABLE V

| Time on-stream, hrs. | Conversion (wt. %) | Selectivity to C$_8$'s (wt. %) |
|---|---|---|
| 6.8 | 99.90 | 21.60 |
| 17.3 | 99.69 | 26.49 |
| 24.9 | 99.38 | 29.64 |
| 30.8 | 97.83 | 35.31 |
| 64.7 | 38.60 | 72.38 |
| 97.8 | 5.78 | 83.91 |
| 102.9 | 7.12 | 73.02 |
| 113.4 | 39.22 | 87.65 |
| 120.9 | 85.45 | 69.17 |
| 127 | 92.16 | 65.89 |
| 137.5 | 94.84 | 62.97 |
| 145.5 | 96.49 | 58.91 |

EXAMPLE V

I. Control

A feed comprising 10% 1-butene in isopentane was oligomerized by the following process: 8 grams of an H-Mordenite 40 catalyst which was treated with zinc nitrate as described in Example IV was placed into a cylindrical reactor tube. The feed was then passed from a feed pump to a series of two guard beds, which contained a 3 Å sieve, silica gel, and a 13× sieve. The feed then passed into the reactor tube, where it then underwent oligomerization and was afterwards collected in a collection vessel. The reaction system ran for about 145 hours. The results are shown in Table VI below.

TABLE VI

| Time on-stream, hrs. | Conversion (wt. %) | Selectivity to C$_8$'s (wt. %) | Selectivity to C$_{12}$'s (wt. %) | Selectivity to C$_{16}$'s (wt. %) |
|---|---|---|---|---|
| 5.6 | 84.76 | 58.66 | 31.00 | 10.33 |
| 16.4 | 82.41 | 64.81 | 27.22 | 7.97 |
| 23.9 | 81.49 | 64.11 | 26.00 | 9.90 |
| 29.6 | 80.78 | 64.02 | 26.01 | 9.97 |
| 95.9 | 76.28 | 72.34 | 24.54 | 3.11 |
| 98.2 | 67.69 | 70.75 | 23.44 | 5.81 |
| 102.4 | 67.28 | 67.16 | 25.68 | 7.16 |
| 118.6 | 88.75 | 53.82 | 31.22 | 14.96 |
| 126.6 | 88.24 | 48.34 | 28.14 | 23.52 |
| 142.6 | 88.24 | 53.25 | 28.39 | 18.37 |
| 145 | 92.02 | 43.66 | 27.58 | 28.76 |

II. Inventive

A feed comprising 10% 1-butene and 1% isobutene in isopentane was oligomerized by the following process: 8 grams of an H-Mordenite 40 catalyst which was treated with zinc nitrate as in Example V was placed into a cylindrical reactor tube. The feed was then passed from a feed pump to a series of two guard beds, which contained a 3 Angstrom sieve, silica gel, and a 13× sieve. The feed then passed into the reactor tube, where it then underwent oligomerization and was afterwards collected in a collection vessel. The reaction system ran for about 145.8 hours. The results are shown in Table VII below.

TABLE VII

| Time on-stream, hrs. | Conversion (wt. %) | Selectivity to C$_8$'s (wt. %) | Selectivity to C$_{12}$'s (wt. %) | Selectivity to C$_{16}$'s (wt. %) |
|---|---|---|---|---|
| 6.8 | 87.38 | 42.91 | 30.76 | 26.33 |
| 17.6 | 94.54 | 43.29 | 27.14 | 29.57 |
| 24.6 | 95.76 | 44.30 | 30.01 | 25.69 |
| 31.2 | 96.99 | 39.90 | 29.34 | 30.76 |
| 41.6 | 98.12 | 39.93 | 32.21 | 27.86 |
| 48.9 | 98.87 | 36.10 | 30.35 | 33.55 |
| 55 | 99.34 | 35.91 | 30.43 | 33.66 |
| 65.9 | 99.25 | 37.88 | 32.52 | 29.60 |
| 73.8 | 99.06 | 35.50 | 29.20 | 35.29 |
| 78.8 | 98.87 | 39.42 | 31.09 | 29.49 |
| 113.3 | 98.31 | 45.09 | 31.55 | 23.35 |
| 145.8 | 98.21 | 37.56 | 27.67 | 34.77 |

Reasonable variations, modifications, and adaptations may be made within the scope of this disclosure and the appended claims without departing from the scope of this invention.

That which is claimed:

1. A process comprising:
   (1) separating a hydrocarbon stream in a separation zone to provide a separated product comprising olefins;
   (2) contacting said olefins with at least one guard bed to provide pretreated olefins, wherein said guard beds contain a compound selected from the group consisting of a 3 Angstrom molecular sieve, silica gel and a 13X sieve,
   (3) contacting said pretreated olefins with a catalyst comprising a zeolite in an oligomerization zone under oligomerization reaction conditions to form an oligomerization product; and
   (4) recovering said oligomerization product;
   wherein the reid vapor pressure of the hydrocarbon stream is higher than the reid vapor pressure of the oligomerization product and a feed comprising 10 wt% 1-butene and 1 wt% isobutene in isopentane would have greater than 99% conversion at 55 hours with a selectivity to C$_8$ of 35.91 wt% wherein said zeolite is treated with a compound comprising a metal selected from the group consisting of tin prior to said contacting with said olefins in step (3).

2. A process in accordance with claim 1 wherein said zeolite has a molar ratio of $SiO_2$ to $Al_2O_3$ in its crystalline framework in the range of from about 10:1 to about 150:1.

3. A process in accordance with claim 1 wherein said zeolite has a molar ratio of $SiO_2$ to $Al_2O_3$ in its crystalline framework in the range of from about 30:1 to about 100:1.

4. A process in accordance with claim 1 wherein said zeolite is a mordenite.

5. A process in accordance with claim 1 wherein said zeolite is mordenites having a silica to alumina molar ratio of 40:1.

6. A process in accordance with claim 1 wherein said zeolite is mordenites having a silica to alumina molar ratio of 90:1.

7. A process in accordance with claim 1 wherein said zeolite is promoted with hydrogen.

8. A process in accordance with claim 1 wherein said olefins have in the range of from 2 to 20 carbon atoms per molecule.

9. A process in accordance with claim 1 wherein said olefins have in the range of from 3 to 6 carbon atoms per molecule.

10. A process in accordance with claim 1 wherein said olefins have in the range of from 4 to 5 carbon atoms per molecule.

11. A process in accordance with claim 1 wherein said olefins have 4 carbon atoms per molecule.

12. A process in accordance with claim 1 wherein said olefins have 5 carbon atoms per molecule.

13. A process in accordance with claim 1 wherein said oligomerization reaction conditions include a temperature in the range of from about 35° C. to about 260° C.

14. A process in accordance with claim 1 wherein said oligomerization reaction conditions include a temperature in the range of from about 65° C. to about 150° C.

15. A process in accordance with claim 1 wherein said oligomerization reaction conditions include a temperature in the range of from 90° C. to 130° C.

16. A process in accordance with claim 1 wherein said olefins are contacted with one to four separate guard beds in step (2).

17. A process in accordance with claim 1 wherein said at least one guard bed is regenerated by a process comprising the steps of: (a) contacting a regeneration stream with said guard bed to form an adsorbed stream; (b) condensing said adsorbed stream to form a condensed stream; (c) adding water to said condensed stream to form a waste stream; and (d) disposing of said waste stream.

18. A process in accordance with claim 17 wherein said regeneration stream is air.

19. A process in accordance with claim 17 wherein said regeneration stream is a gaseous organic compound.

20. A process in accordance with claim 19 wherein said gaseous organic compound is gaseous isobutane.

21. A process in accordance with claim 1, further comprising regenerating said catalyst in a regeneration zone under regeneration conditions.

22. A process in accordance with claim 21 wherein said regeneration conditions comprise contacting said catalyst with a regeneration stream selected from the group consisting of nitrogen, air, supercritical isobutane, and light hydrocarbons.

23. A process in accordance with claim 21 wherein said regeneration conditions further comprise a temperature in the range of from about 50° C. to about 900° C.

24. A process in accordance with claim 1, further comprising: (4) separating compounds comprising n-alkenes from said oligomerization product; (5) contacting said compounds comprising n-alkenes with an isomerization catalyst in an isomerization reaction zone under isomerization conditions to form an isomerization product; and (6) returning said isomerization product to said oligomerization zone.

* * * * *